(12) United States Patent
Cummings

(10) Patent No.: US 7,981,680 B2
(45) Date of Patent: Jul. 19, 2011

(54) METHOD FOR ANALYZING PETROLEUM-BASED FUELS AND ENGINE OILS FOR BIODIESEL CONTAMINATION

(75) Inventor: Jill M. Cummings, Bay City, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 290 days.

(21) Appl. No.: 12/268,619

(22) Filed: Nov. 11, 2008

(65) Prior Publication Data
US 2010/0120158 A1    May 13, 2010

(51) Int. Cl.
*G01N 31/00*    (2006.01)
(52) U.S. Cl. .......................................... 436/60; 436/161
(58) Field of Classification Search ............ 436/60, 436/161; 73/53.05
See application file for complete search history.

(56) References Cited

U.S. PATENT DOCUMENTS

2010/0116022 A1 *    5/2010    Cummings ................. 73/23.41
* cited by examiner

*Primary Examiner* — Jill Warden
*Assistant Examiner* — Dwan A Gerido
(74) *Attorney, Agent, or Firm* — Harness, Dickey & Pierce, P.L.C.

(57) ABSTRACT

A method for detecting contamination of a conventional petroleum-based fuel used in an internal combustion engine is provided. A sample of engine oil is separated into a polar component and a non-polar component by a polar solvent. The polar component is analyzed for one or more biodiesel chemical components selected from the group consisting of plant sterols, fatty acid methyl esters, cetane, and combinations thereof, which relate to a degree of engine oil contamination. The polar and non-polar component may be analyzed by Gas Chromatography and Mass Spectrometry (GC/MS) and optionally Flame Ionization Detection (FID) for the one or more biodiesel chemical components, which can provide a semi-quantitative level of such biodiesel chemical components. Fuel samples can also be analyzed for biodiesel contamination species via GC/MS.

14 Claims, 2 Drawing Sheets

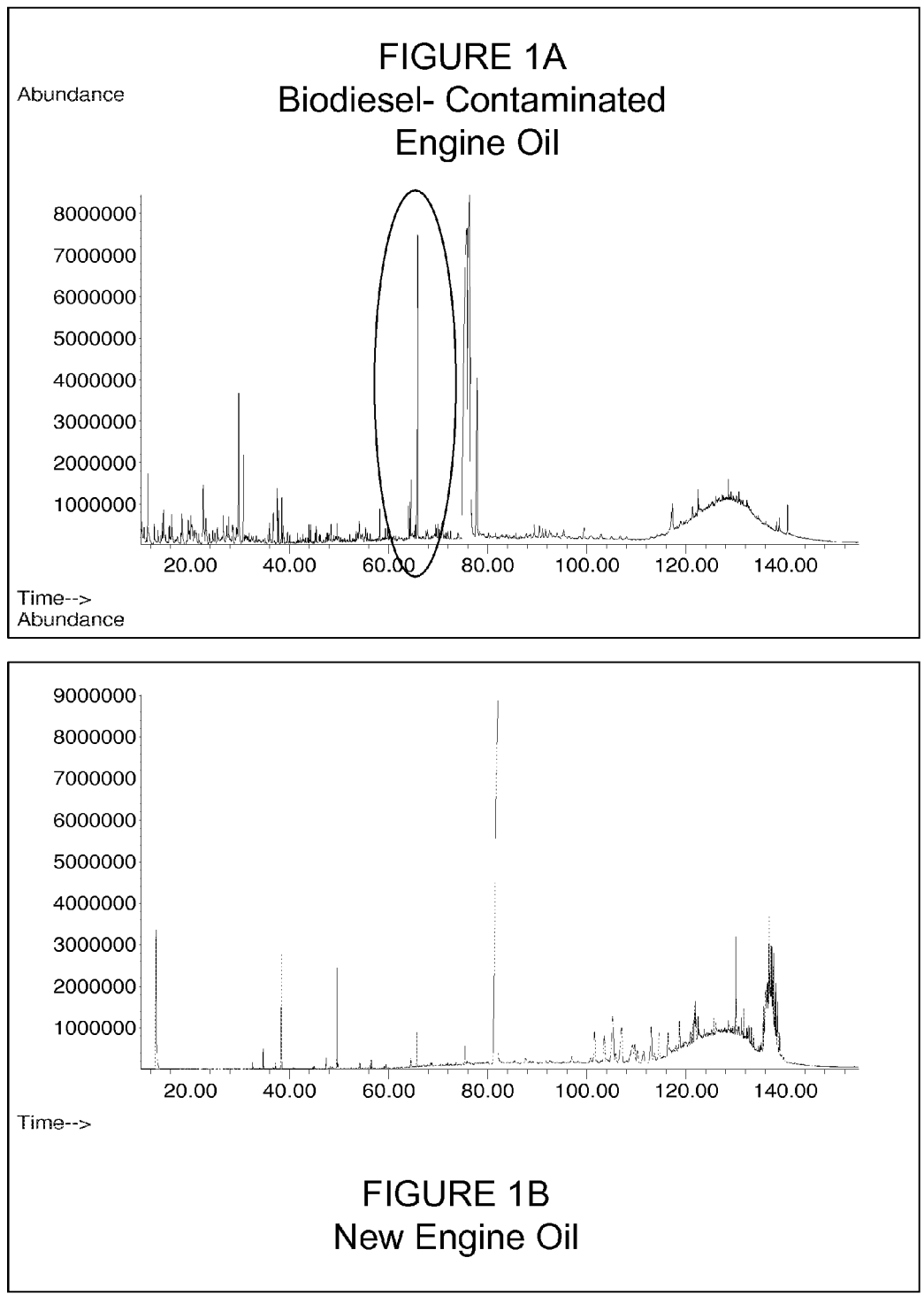

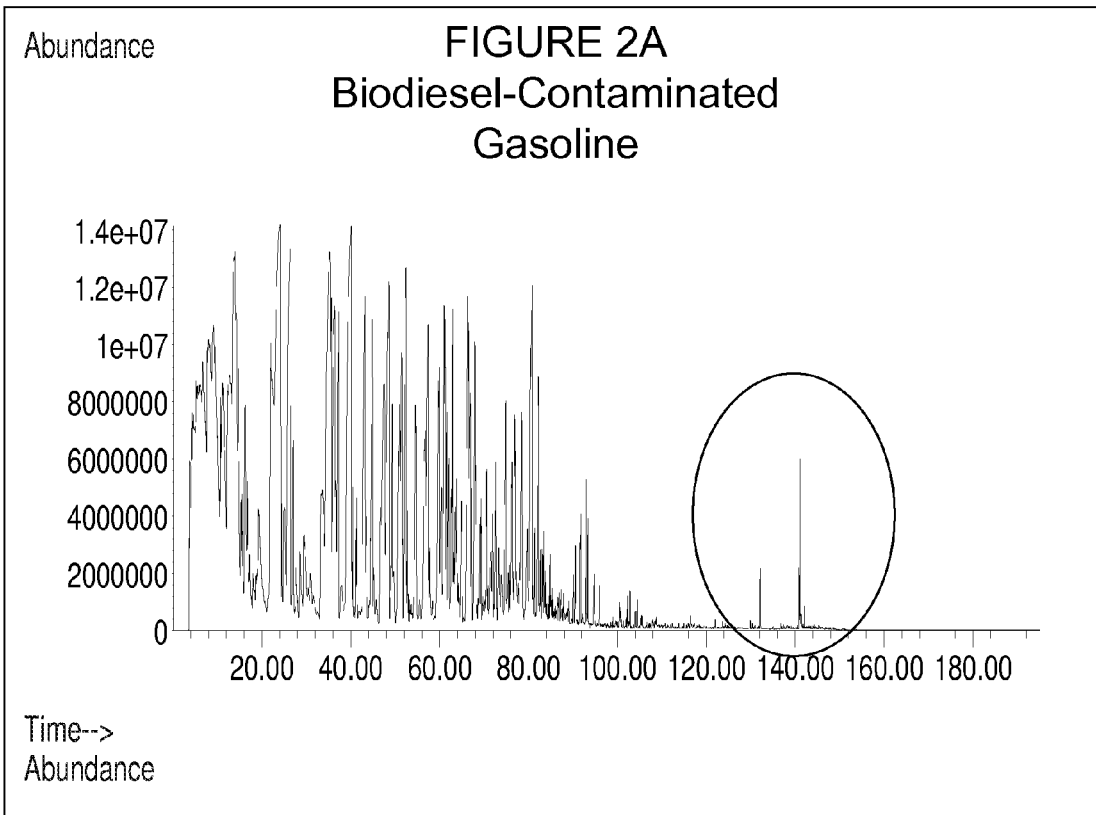
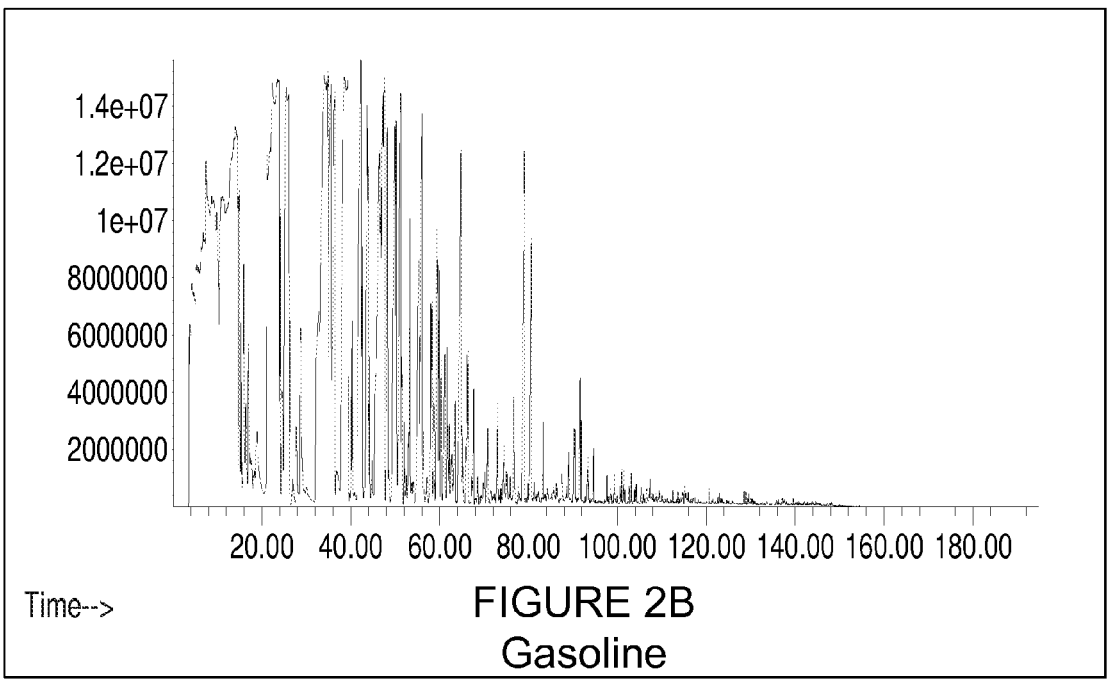

METHOD FOR ANALYZING PETROLEUM-BASED FUELS AND ENGINE OILS FOR BIODIESEL CONTAMINATION

FIELD

The present disclosure relates to a method for analyzing fuel contamination, and more particularly for detecting a level of contamination in engine oil, gasoline, or diesel fuel for the presence of biodiesel chemical components.

BACKGROUND

This section provides background information related to the present disclosure which is not necessarily prior art.

Biofuels are obtained from a renewable source, such as biological sources like animal or vegetable materials, and are thus regarded as being more "environmentally-friendly" than petroleum-based fuels. Biodiesel fuels are increasingly being used for internal combustion (e.g., spark igniter) engines designed to consume such biofuels. When a biofuel, such as biodiesel, is used in an internal combustion engine designed to consume petroleum-based fuels like gasoline; however, multiple engine components could fail, resulting in potential failure of the engine and all of the fuel system hardware. Similar issues may occur where a diesel fuel is used in an engine designed to consume gasoline.

Thus, diesel or biodiesel contamination for an internal combustion engine that is not specifically designed to consume such fuels may cause plugged filters, improper compression pressure temperature, reduced catalytic converter efficiency and life, vehicle stalling, and poor driveability. As such, for diagnostic purposes, it can be desirable to determine or measure the presence of biodiesel or diesel fuel (e.g., contamination) in a gasoline fuel and in the engine oil used in a suitable internal combustion engine.

SUMMARY

In various aspects, the present disclosure provides a method for detecting biodiesel contamination of a conventional petroleum-based fuel used in an internal combustion engine. In certain aspects, the method comprises detecting contamination of a gasoline fuel by detecting one or more biodiesel chemical components in an engine oil sample from the internal combustion engine or in a fuel sample itself.

In certain aspects, an engine oil sample is separated into a polar component and a non-polar component and analyzed for one or more biodiesel chemical components. Such biodiesel chemical components are related to the presence of either biodiesel or diesel fuels in conventional gasoline fuels. The method comprises detecting one or more biodiesel chemical components selected from the group consisting of plant sterols, fatty acid methyl esters, cetane, and combinations thereof. In certain aspects, the engine oil sample is admixed with a polar solvent to form a mixture, where the mixture is agitated and permitted to settle for at least 18 hours, optionally about 24 hours for suitable separation. The method comprises extracting the polar component with a polar solvent. In certain aspects, the polar solvent has a polarity index greater than or equal to 5. In other aspects, the polar solvent is an alkanol having 1 to 4 carbon atoms. In certain aspects, the polar solvent comprises methanol. The method also comprises analyzing the polar component by Gas Chromatography and Mass Spectrometry (GC/MS) and optionally by Flame Ionization Detection (FID).

In other aspects, the present disclosure pertains to detecting the presence of biodiesel in a conventional petroleum-based fuel for an internal combustion engine, like gasoline or diesel fuel. Such a method comprises detecting one or more biodiesel chemical components in a sample of an engine oil or fuel used in the internal combustion engine, which is designed to consume the petroleum-based fuel. In certain aspects, the oil sample is separated into a polar component and a non-polar component via extraction with a polar solvent, such as a polar solvent having a polarity index greater than or equal to 5. The polar component of the engine oil sample is then analyzed for one or more of the biodiesel chemical components.

In yet other aspects, the method further comprises detecting a second amount of one or more biodiesel chemical components related to the presence of one or more biodiesel chemical components in a second sample of a second engine oil, which is distinct from the first engine oil. The second engine oil sample is separated into a polar component and a non-polar component via extraction with a polar solvent having a polarity index greater than or equal to 5. The polar component is analyzed and the second sample is distinct from the first sample. In this regard, the first amount of one or more biodiesel chemical components can be compared to the second amount for one of one or more biodiesel chemical components to detect the relative presence of engine contamination of the first engine oil sample, as compared to the second engine oil sample. In certain aspects, the method includes determining a semi-quantitative difference between the first biodiesel chemical components and the second biodiesel chemical components, for example, by semi-quantitative analysis of Mass Spectrometry results after Gas Chromatography processing optionally combined with by a quantitative method like Flame Ionization Detection (FID).

In certain aspects, the present disclosure provides a method for detecting an alternative fuel contaminant in a conventional petroleum-based fuel, such as gasoline or diesel fuel. The method includes analyzing a fuel sample by Gas Chromatography and Mass Spectrometry (GC/MS) for the presence of one or more biodiesel chemical components selected from the group consisting of plant sterols, fatty acid methyl esters, cetane and combinations thereof.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1A-B show comparative analysis of gas chromatography and mass spectrometry analysis via a total ion chromatogram or TIC, of an engine oil tested for and having biodiesel contamination (FIG. 1A) as compared to a new engine oil (FIG. 1B); and FIGS. 2A-2B show comparative analysis of gas chromatography and mass spectrometry analysis via a total ion chromatogram of a biodiesel contaminated gasoline fuel sample (FIG. 2A) as compared to a baseline uncontaminated gasoline-based fuel (FIG. 2B).

Corresponding reference numerals indicate corresponding parts throughout the several views of the drawings.

DETAILED DESCRIPTION

In various aspects, the present disclosure provides a method for detecting contamination of a petroleum-based fuel used in an internal engine combustion engine by using either a sample of engine oil from an internal combustion engine that was fueled by a potentially contaminated petroleum-based fuel, or in alternate aspects, by testing the subject fuel itself for contamination. The petroleum-based fuel may be gasoline, for example. In certain aspects, an engine oil sample is separated into a polar component and non-polar component. The polar component is then analyzed for one or more biodiesel chemical components selected from a group consisting of plant sterols, fatty acid methyl esters, and combinations thereof. In alternate aspects, in the case of gasoline fuels, the polar component may be analyzed for one or more diesel fuel chemical components, such as cetane and/or for biodiesel components, such as plant sterols, fatty acid methyl esters, and the like.

While biodiesel is typically suitable for use in an internal combustion engine designed to consume diesel, it is usually not suitable for use in an internal combustion engine designed to consume gasoline. Further, gasoline engines are typically incapable of consuming conventional diesel fuels, as well. Gasoline generally refers to petroleum-derived liquid mixture consisting mostly of aliphatic hydrocarbons, enhanced with iso-octane or the aromatic hydrocarbons toluene and benzene. Gasoline typically contains a mixture of various hydrocarbon compounds, various organic compounds, including straight and branched chain paraffins, olefins, aromatics and naphthenic hydrocarbons, and other liquid hydrocarbonaceous materials suitable for spark ignition internal combustion engines. Diesel includes a large proportion (about 75% of greater) of saturated hydrocarbons (including paraffins and hexadecane or cetane ($C_{16}H_{34}$)) and a smaller proportion of aromatic hydrocarbons (including naphthalene and alkylbenzene). Conventional petroleum-based diesel fuels frequently comprise cetane, which is absent gasoline, as will be described in greater detail below.

Biodiesel (or "alternative fuel") refers to a variety of ester-based fuels (e.g., fatty esters) generally made from plant sources, such as vegetable oils, like soybean oil, canola or hemp oil, or from animal sources, like animal fats, by way of non-limiting example. Thus, biodiesel includes a class of fuels derived from biological sources, including plant and animal sources, which includes plant-based oil derivatives that are hydrolyzed to release triglycerides, free fatty acids, or other substances, which are then converted to fuel additives useable as fuels, like mono-alkyl esters. Biodiesel fuels are typically mixed with petroleum-based diesel fuels. Other alternative fuels include biofuels that contain alcohols like ethanol, which can be made from plant-sources, including grains like corn, barley, sorghum, and wheat that contain high starch levels, can be broken down into sugars needed for traditional fermentation and conversion to ethanol or other alcohols, which is then used as a fuel. Other non-limiting sources of alcohols for biofuels are cellulose-based and/or lignocellulose-based plant matter, like switch grass, corn stalks, wheat stalks, agricultural, municipal, paper industry, and forestry waste products.

In certain aspects, a method for detecting contamination of a gasoline-based fuel used in an internal engine combustion engine is provided by taking an engine oil sample used in the engine, which is then separated into a polar component and non-polar component. In various aspects, the separating comprises extracting the polar component with a polar solvent. In certain aspects, the polar solvent is an alkanol having 1 to 4 carbon atoms, such as methanol, ethanol, n-propanol, iso-propanol, and n-butanol, t-butanol, iso-butanol, and the like. In certain aspects, the polar solvent has a polarity index greater than or equal to 5. By way of example, a preferred polar solvent comprises methanol ($CH_3OH$), which has a polarity index of about 5.1. A suitable methanol is commercially available at 99.95% purity (e.g., a pesticide grade having trace amounts of any other impurities). Other suitable examples of polar solvents include acetone having a polarity index of about 5.1 and 2-methoxy ethanol having a polarity index of about 5.5. In certain alternate aspects, the polar solvent may include combinations of different compounds, so that the solvent mixture or solution has the desired polarity. For example, in certain alternate embodiments, a mixture of polar solvents may have a polarity index of greater than or equal to 5.

In various aspects, separating comprises admixing the engine oil sample with a polar solvent to form a mixture. A mixture can be a solution of the engine oil sample, the polar solvent, along with any debris present, so that the admixing of the components is generally a solubilizing process. In certain aspects, the mixture (e.g., solution) is then agitated. In yet other aspects, the application of heat is avoided to minimize potential evaporation of solvent, thus changing the volume/concentration of the mixture (e.g., solution). The mixture (e.g., solution) can be agitated by shaking, rolling, inverting, sonication or using an automated shaker. In certain aspects, the mixture (e.g., solution) is permitted to settle to achieve adequate separation into the polar and non-polar components. By way of example, a 1 ml engine oil sample is mixed with 9 ml of methanol. The mixture (e.g., solution) is permitted to settle for at least 18 hours, preferably about 24 hours to achieve 90-95% separation into a polar component and non-polar component and to remove any solid debris or metallic compounds in the used sample. As appreciated by those of skill in the art, the time permitted for separation may vary depending on the volume of the sample to be separated.

In various aspects, the method of detecting biodiesel presence in a gasoline-based fuel comprises analyzing the polar component of the engine oil sample for one or more diesel chemical components, including biodiesel chemical components or diesel fuel chemical components. Certain biodiesel/diesel chemical components of the present disclosure are extracted into the polar phase in accordance with the present teachings. Thus, the presence of one or more biodiesel chemical components in the engine oil polar component provides information as to whether the fuel consumed by the engine is contaminated with a biodiesel fuel. For example, fatty acid methyl esters are one indicator species of biodiesel fuel contamination that can be extracted into the polar component for analysis. Biodiesel typically comprises fatty acid methyl esters of saturated, monounsaturated, and polyunsaturated fatty acids having at least $C_{18}$, optionally having greater than or equal to about $C_{20}$, e.g., $C_{18}$-$C_{25}$ fatty acids. Engine oil contains fatty acid methyl esters in the range of $C_{14}$ to $C_{20}$. Fatty acid methyl esters greater than $C_{20}$ are typically found in a biodiesel and thus are used in accordance with the present teachings to indicate the presence of biodiesel contamination in an engine using a conventional petroleum-based fuel.

Non-limiting examples of fatty acid methyl esters found in biodiesels include esters of palmitic acid, heptadecylic acid, stearic acid, nonadecanoic acid, arachidic acid, behenic acid, lignoceric acid, cerotic acid, heptacosanoic acid, montanic acid, melissic acid, lacceric acid, crotonic acid, isocrotonic acid, undecylenic acid, oleic acid, elaidic acid, cetoleic acid, erucic acid, brassidic acid, sorbic acid, linoleic acid, linolenic acid, arachidonic acid, propiolic acid, stearolic acid, nervonic acid, licinoleic acid, (+)-hydnocarpic acid, (+)-chaulmoogric acid, and combinations thereof.

Biodiesel often contains sterols derived from plants, as well. Non-limiting examples of such plant sterols include stigmasterol, campesterol, rapeseed oil, coriander oil, soya oil, cottonseed oil, sunflower oil, castor oil, olive oil, peanut oil, maize oil, almond oil, palmseed oil, coconut oil, mustard-seed oil, bovine tallow, bone oil and fish oils. Further examples include oils which are derived from wheat, jute, sesame, shea tree nut, arachis oil and linseed oil.

In the present disclosure, cetane is a diesel fuel chemical component, which can be an indicator of the contamination of a gasoline fuel with diesel fuel. Further, petroleum-based diesel fuel is generally mixed with biodiesel fuels and thus, cetane is present in biodiesel fuels, as well. The cetane number is a measure for the ignition quality of intermediate distillates, particularly in biodiesel fuel or diesel fuel. Typically cetane numbers range from 0 to 100. Cetane is typically present in any diesel based fuel. For example, North American diesel typically has a cetane number of 40, whereas European diesel has a cetane number ranging from 45 to 48.

In certain aspects, the polar component is analyzed by gas chromatography and then mass spectrometry (GC/MS) to find one or more chemical components. Gas chromatography is a method for isolating a sample by its components before it is delivered to a detector for detection. In certain aspects, the interior walls of the gas chromatograph column are coated with a material commonly referred to as a stationary phase. The stationary phase retains the various components of the injected sample and, through the application of heat, releases the components so that they are received by the detector separated in time. In various aspects, the gas chromatography column comprises (5%-Phenyl)-methylpolysiloxane for the analysis of the polar component.

As is known in the art, heavier components require more heat and/or more time to elute from the column than do lighter components. In various aspects, analyzing comprises heating the polar component to a predetermined temperature during the gas chromatography. By way of example, in certain aspects, heating the polar component to about 75° C. separates the polar solvent. The 75° C. temperature is held for a certain period, e.g., 5 minutes, and then a moderate temperature ramp is applied to further separate the fatty acid methyl esters. Heating up to 200° C. (ramping) isolates or separates any low molecular weight fatty acid methyl esters that may be present in the polar component. In certain aspects, the sample in the column is heated to a predetermined temperature, for example, to about 200° C. for about 45 minutes. The higher temperature separates the higher molecular weight amine compounds and plant sterols. In certain aspects, analyzing further comprises heating the polar component to a second predetermined temperature (following the heating to the first predetermined temperature). For example, in certain preferred embodiments, a second predetermined temperature is about 310° C., which is held for greater than or equal to about 20 minutes, e.g., about 22 minutes, for separating the sterol compounds of interest. For example, during the ramp up to 310° C., plant sterols are preferably separated.

In various aspects, the detector for the analysis step is mass spectrometry. In various aspects, analyzing the elute of the polar component comprises the mass spectrum of signal strength data as a function of mass-to-charge ratio. In a mass spectrum, the signal strength data may be in the form of peaks on a chromatogram of signal intensity as a function of mass-to-charge ratio. The intensity of the peak is also generally associated with the apex of the peak. Generally, the mass-to-charge ratio relates to the molecular weight of a potential marker.

In yet other aspects, the detector for the analysis step further comprises Flame Ionization Detector (FID) analysis. The FID provides a series of peaks on the chromatogram and provides a quantitative amount of the species present. In certain aspects, the FID analysis is optionally used along with mass spectrometry analysis, to employ a mass spectra library via the MS that can positively identify the chemical species (e.g., carbon chain length of the esters or the plant sterol). Thus, in certain aspects the analysis includes GC/MS and FID of the sample.

In various aspects, the present disclosure provides a method for detecting one or more biodiesel chemical components in an engine oil sample used in the internal combustion engine which is designed to consume a petroleum-based fuel, which relates to the presence of biodiesel chemical components in the fuel. The engine oil sample is separated into a polar component and a non-polar component via extraction with a polar solvent. For example, a polar solvent having a polarity index greater than or equal to 5 is particularly suitable. Then, at least one of the polar component or the non-polar component is analyzed for one or more biodiesel chemical components. In certain aspects, the methods of the present disclosure are particularly useful for failure analysis techniques, to determine the cause of engine malfunction or failure by taking a sample of engine oil from the subject engine for testing to determine whether a fuel used in the engine was contaminated with an unsuitable fuel.

In yet other aspects aspects, the methods of the present disclosure can be used for comparative testing information and engine or oil design. By way of example, in certain methods, the engine oil sample is a first sample of a first engine oil and detecting provides a first amount of one or more biodiesel chemical components. The method also comprises detecting a second amount of one or more biodiesel chemical components related to the presence of one or more biodiesel chemical components in a second sample of a second engine oil, which is compositionally distinct from the first engine baseline oil. The second sample is similarly separated into a polar component and a non-polar component via extraction with a polar solvent, such as a polar solvent having a polarity index greater than or equal to 5. Then, at least one of the polar component or the non-polar component for the second sample is analyzed for one or more biodiesel chemical components. The polar component of the second sample is analyzed to determine the second amount of the one or more biodiesel contaminants, which relate to a degree of contamination of the second engine oil composition. As noted above, analysis of the second polar component of the second sample is conducted in certain embodiments by Gas Chromatography followed by Mass Spectrometry for one or more biodiesel chemical components.

The second engine oil sample is distinct from the first engine oil sample. By "distinct," it is meant that the engine oil samples may be the same formulation, for example, a specific commercially available brand of engine oil, where the first engine oil sample is new and the second engine oil sample has been used in an engine for a specific duration of time. Different oil samples may also be entirely different engine oils that are compared for relative performance in an internal combustion engine. In certain aspects, an engine oil sample is a new engine oil sample, wherein "new" is defined as a sample that has not been exposed to oxidation, contamination, and/or physical wear. In certain aspects, an engine oil sample is a used or old engine oil sample, meaning that the sample has been exposed to oxidation, contamination, and/or physical wear.

The first amount of one or more biodiesel chemical components is then compared to the second amount of one or more biodiesel chemical components. In certain aspects, determining an amount of one or more biodiesel contaminants may simply be detecting the presence or absence of such biodiesel contaminants species, without quantification or semi-quantification. In other aspects, determining means that the amount of one or more biodiesel contaminants is quantified or semi-quantified. In certain aspects, the amount of one or more biodiesel contaminants is semi-quantified by integration of a mass specification analysis by comparing integrated peak areas. Such semi-quantification can be compared against a calibration curve, or a known reference or database of values. In embodiments where FID is used for additional analysis, quantification of the amount of diesel chemical compound indicators is also contemplated.

In various aspects, comparing the first amount of the one or more biodiesel contaminants to the second amount of the one or more biodiesel contaminants includes semi-quantifying the relative presence of biodiesel chemical components of the first engine oil sample as compared to the second engine oil sample. By way of example, the integrated peak area for fatty acid methyl esters and plant sterols in a biodiesel sample can be plotted on a calibration curve. For example, 5% biodiesel fuel and 20% biodiesel fuel are plotted with the areas of the stigmasterol or campesterol at the specific retention times to determine the range of peak areas found. A pure diesel sample should not contain this peak. When an engine oil sample is tested, the peak area at this specific retention time can be overlaid on the plotted chromatogram by the GC/MS software and the peak areas are compared for the difference between the values (delta).

In certain variations, the presence of one or more biodiesel chemical components is compared between a first engine oil sample and a second engine oil sample, which provides general information about the engine oil contamination. Further, in certain variations, the first and second amounts of one or more biodiesel chemical components are compared with one another to provide additional information about the comparative engine oil contamination. In other variations, the comparing of the first and second engine oil samples may include establishing a baseline level for the presence or absence of one or more of the biodiesel chemical components.

In certain alternate aspects, the present disclosure provides a method for detecting an alternative fuel contaminant in a gasoline-based fuel. The method comprises analyzing a fuel sample for the presence of biodiesel chemical components from the group consisting of plant sterols, fatty acid methyl esters, cetane and combinations thereof. The analysis is conducted via Gas Chromatography followed by Mass Spectrometry (GC/MS). In certain aspects, the fuel sample is directly injected into the gas chromatograph (without admixing with a polar solvent to separate into polar and non-polar components). In various aspects, analyzing comprises heating the fuel sample to a predetermined temperature during the gas chromatography. For example, a temperature of 35° C. optionally burns off any ethanol that may be present in the gasoline.

A slow heating rate (slow temperature ramp) serves to separate the hydrocarbons and combustion products from the sample. In various aspects, the heating to a predetermined temperature is heating to about 100° C. for about 1 minute. Another slow temperature ramp separates the middle to higher temperature hydrocarbons and combustion products from the fuel sample. In various aspects, analyzing further comprises heating the fuel sample to a second predetermined temperature after the first predetermined temperature, wherein the second predetermined temperature is about 200° C. for about 1 minute. This temperature ramp separates higher temperature hydrocarbons and the higher molecular weight fatty acid methyl esters. In various aspects, analyzing further comprises heating the sample to a third predetermined temperature after the second predetermined temperature wherein the third predetermined temperature is about 310° C. The heating can be done at 310° C. for about 40 minutes. For example, the third predetermined temperature separates any remaining high molecular weight hydrocarbons and high molecular weight esters and higher molecular weight plant sterols.

The fuel sample is then analyzed for one or more biodiesel chemical components selected from the group consisting of plant sterols, fatty acid methyl esters, and combinations thereof. Exemplary biodiesel chemical components include stigmasterol, campesterol, methyl heptadecanoate, arachidic acid methyl ester, behenic acid methyl ester, gadoleic acid methyl ester, lignoceric acid methyl ester, erucic acid methyl ester, soybean plant phytosterol, rapeseed plant phytosterol and combinations thereof.

EXAMPLE 1

Example 1 analyzes an engine oil sample with GC/MS. 20 ml of pesticide grade heptane (99.95% purity) is poured into a 150 ml beaker and is used to clean glassware. 20 ml of heptane is poured into another 150 ml beaker and covered and 20 ml of methanol is poured into another 150 ml beaker and covered. A 10 ml thimble is placed into Wheaton vial rack upside down to dry from rinsing. The engine oil sample is placed in a sample bottle for 30 seconds and shaken from end to end. Then sample bottle is rolled back and forth for 30 seconds. In the alternative, the engine oil sample can be placed on an automated shaker at medium speed and shaken for 1 minute. Next, the bottom of the sample bottle is checked for any sediment and/or debris. If sediment is present, the sample is shaken until the sediment is gone.

Using a plastic transfer pipette, 1 ml of engine oil is placed into a thimble. The plastic transfer pipette is held straight to ensure oil meniscus is level with the 1 ml increment line. Next, 9 ml of methanol is poured into the thimble and the volume is brought up to 10 ml with the solvent meniscus level with the 10 ml increment line. In preferred aspects, solvents are handled with glassware, rather than plastics to prevent the leaching of any plasticizers or stabilizers such as phthalates which may show up on the chromatogram analysis. The inversion and shaking is repeated for a total of 2 minutes. The bottom of thimble is ensured to be free from any oil residue and the mixture (e.g., solution) appears homogeneous. The solution is poured into an 11 ml scintillation vial, labeled, and placed in Wheaton vial tray upright.

The 11 ml vials are permitted to settle for 24 hours in the rack. The oil and methanol solution separates into multiple phases. After the vials have settled for 24 hours, a glass transfer Pasteur pipette is used to place 2 ml of the very top layer of the methanol solution into a 2 ml GC vial. Next, the GC vial cap is crimped and placed in GC/MS autosampler tray. The 11 ml vials are capped and all remaining solutions are refrigerated in storage for up to 30 days. All glassware is triple rinsed with the heptane and methanol solvents, inverted and air dried.

The gas chromatography column type is commercially available from Agilent as DB5MS-HT used in a 6890 Agilent GC column. The mass spectrometer is 5975 MS. The column dimensions are 60 m×0.25 mm×0.25 μm. The injection type selected is automatic (AUTO), where the solvent delay is 10 min. The inlet temp is 275° C., the transfer temp is 300° C., and the initial oven temperature is 75° C. The initial time hold is at the initial over temperature occurs for about 5 minutes. A first rate of oven heating (Rate 1) is 2° C./min; a first temperature (Temp 1) is about 200° C. and held for a duration (Hold 1) is about 45 minutes. A second heating rate (Rate 2) is 5° C./min; where a second predetermined temperature (Temp 2) is 310° C., and a second hold duration (Hold 2) is about 22.5 min. The total run time is 157 min. The mode is pulsed splitless. The gas type is Helium. The column flow for the GC analysis is 2 ml/min. The injection volume is 1 μl. The low scan mass is 15 Daltons (Da) and the high scan mass is 900 Da. The EM voltage is 1300-1400 volts. The MS integration parameters for data interpretation initial area reject are 800,000. The initial peak width is 0.15. The shoulder detection is off. The initial threshold is 18.

The GC columns are selected to be low bleed columns. A maximum operating temperature is selected to be about 325-330° C., where methylene chloride blanks are run in between every sample for cleaning of the syringe and column. Methylene chloride is used as the wash solvent for the instrument set-up. The high end point temperature elutes the plant sterol peaks and separates methyl esters present in plant sterol peaks from those commonly used in engine oil formulations of $C_{18}$ or less. The biodiesel methyl ester contaminants are generally $C_{19}$-$C_{25}$.

An engine oil sample, commercially available from ExxonMobil as MobilClean 5W30 or Rotella 15W40 from Shell, is tested in accordance with the preparation and analysis techniques described above (for GC/MS). A sample is taken when the engine oil is new, prior to use in the internal combustion engine and analyzed in the manner described above to create FIG. 1B. A 50 ml sample of engine oil is taken from an internal combustion gasoline engine operated with an unknown quantity of biodiesel. The sample is tested in the manner described above with the results shown in FIG. 1A. The contamination of one or more biodiesel chemical components, here a fatty acid methyl ester, is indicated around 65, which is absent in FIG. 1B and the heavier fatty acid methyl esters, between 80 and 100 minutes, which are significant markers of the biodiesel esters

EXAMPLE 2

In Example 2, a fuel sample is analyzed with gas chromatography. The fuel is collected in a clean glass container to ensure debris is not in the sample. In preferred aspects, solvents are handled with glassware, rather than plastics to prevent the leaching of any plasticizers or stabilizers such as phthalates which may show up on the chromatogram analysis. The fuel sample does not need any solvent preparation or dilution. A 1 ml glass Pasteur pipette is used to place 2 ml of the fuel into a GC vial and then in the autosampler tray for direct injection into the GC/MS. The instrument parameters are customized to separate light, medium, and heavy hydrocarbons from the esters and plant sterols.

The GC/MS apparatuses are the same as those in Example 1. The injection type is AUTO, where the solvent delay is selected to be 0 minutes. The inlet temperature is about 250° C., the transfer temperature is about 300° C., and the oven initial temp is about 35° C. The initial time hold is 1 minute.

A first rate of oven heating (Rate 1) is 1° C./min; a first temperature (Temp 1) is about 100° C. and a hold duration (Hold 1) is about 1 minute. A second heating rate (Rate 2) is 1.5° C./min; where a second predetermined temperature (Temp 2) is 200° C., and a second hold duration (Hold 2) is about 1 minute. A third heating rate (Rate 3) is 1° C./min; where a third predetermined temperature (Temp 3) is 310° C., and a third hold duration (Hold 3) is about 40 minutes. The total run time is 205 minutes. The mode is pulsed splitless. The gas type is Helium. The column flow is 1 ml/min. The injection volume is 0.2 μl. The low scan mass is 40 Da and the high scan mass is 900 Da. The EM voltage is 1350-1500 volts. The MS integration parameters for data interpretation initial area reject are 800,000. The initial peak width is 0.15. The shoulder detection is off. The initial threshold is 17.

The columns are selected to be low bleed columns as discussed above. A maximum operating temperature is selected to be about 325-330° C. Methylene chloride blanks are run in between every sample for cleaning of the syringe and column. Methylene chloride is used as the wash solvent for the instrument set-up. The high end point temperature elutes the plant sterol peaks and separates methyl esters present and plant sterol peaks which are not present in gasoline or regular diesel fuel. The biodiesel fatty acid methyl ester contaminants are conventionally $C_{19}$-$C_{25}$ or greater.

A gasoline sample, commercially available from Citgo, British Petroleum, and Shell as Regular Unleaded 87 octane, is tested in accordance with the preparation and analysis techniques described above (for GC/MS). The gasoline control sample is analyzed in the manner described above to create FIG. 2B. The warranty or field return sample is likewise tested in the manner described above to create FIG. 2A. In comparing FIGS. 2A and 2B, FIG. 2A indicates the biodiesel plant sterol around 140 minutes. In this manner, the contamination of either gasoline fuel or engine oil from an engine consuming such biodiesel fuel can be easily determined and analyzed in accordance with various aspects of the present teachings.

What is claimed is:

1. A method for detecting contamination of a gasoline fuel used in an internal combustion engine comprising:
    detecting one or more biodiesel chemical components in an engine oil sample from said internal combustion engine, by separating said sample into a polar component and a non-polar component and analyzing at least one of said polar component or said non-polar component for said one or more diesel chemical components, wherein the detecting of said one or more biodiesel chemical components indicates contamination of the gasoline fuel.

2. The method according to claim 1, wherein said separating comprises admixing said engine oil sample with a polar solvent to form a mixture; agitating said mixture; and permitting said mixture to settle for at least 24 hours, wherein said polar solvent has polarity index greater than or equal to 5.

3. The method according to claim 1, wherein said one or more biodiesel chemical components are selected from the group consisting of plant sterols, fatty acid methyl esters, cetane and combinations thereof.

4. The method according to claim 3, wherein said one or more biodiesel chemical components is a biodiesel chemical component selected from the group consisting of stigmasterol, campesterol, methyl heptadecanoate, arachidic acid methyl ester, behenic acid methyl ester, gadoleic acid methyl ester, lignoceric acid methyl ester, erucic acid methyl ester, soybean plant phytosterol, rapeseed plant phytosterol and combinations thereof.

5. The method according to claim 1, wherein said separating comprises admixing said engine oil sample with a polar solvent to form a mixture; agitating said mixture; and permitting said mixture to settle for at least 24 hours, wherein said polar solvent comprises an alkanol having 1 to 4 carbon atoms.

6. The method according to claim 5, wherein said polar solvent comprises methanol.

7. The method according to claim 1, wherein said analyzing comprises injecting said polar component into Gas Chromatography/Mass Spectrometry (GC/MS), wherein a Gas Chromatography column of said GC/MS comprises 5% phenyl-95% dimethylpolysiloxane.

8. The method according to claim 7, wherein said analyzing includes heating said sample during said GC process to a first predetermined temperature of about 200° C. for about 45 minutes.

9. The method according to claim 8, wherein said analyzing further comprises heating said sample to a second predetermined temperature after said first predetermined temperature, wherein said second predetermined temperature is about 310° C. for greater than or equal to about 20 minutes.

10. A method for detecting contamination of a conventional petroleum-based fuel for an internal combustion engine comprising:
   detecting one or more biodiesel chemical components related to the presence of said one or more biodiesel chemical components in a sample of an engine oil used in the internal combustion engine, which is designed to consume a petroleum-based fuel;
   separating said sample into a polar component and a non-polar component via extraction with a polar solvent having a polarity index greater than or equal to 5; and
   analyzing at least one of said polar component or said non-polar component for said one or more biodiesel chemical components, wherein the detecting of said one or more biodiesel chemical components indicates contamination of the conventional petroleum-based fuel.

11. The method according to claim 10, wherein said analyzing comprises Gas Chromatography and Mass Spectrometry (GC/MS) and optionally flame ionization detection (FID).

12. The method according to claim 10, wherein said one or more biodiesel chemical components is selected from the group consisting of coolant, cetane, methyl heptadecanoate, arachidic acid methyl ester, behenic acid methyl ester, gadoleic acid methyl ester, lignoceric acid methyl ester, erucic acid methyl ester, soybean plant phytosterol, rapeseed plant phytosterol, stigmasterol, campesterol, and combinations thereof.

13. The method according to claim 10, wherein said sample of said engine oil is a first sample of a first engine oil and said detecting provides a first amount of said one or more biodiesel chemical components, wherein the method further comprises detecting a second amount of one or more biodiesel chemical components related to the presence of a biodiesel chemical components in a second sample of a second engine oil;
   separating said second sample into a polar component and a non-polar component via extraction with a polar solvent having a polarity index greater than or equal to 5;
   analyzing at least one of said polar component or said non-polar component for said second sample for one or more biodiesel chemical components, wherein said second sample is distinct from said first sample; and
   comparing said first amount of said one or more biodiesel chemical components to said second amount of said one or more biodiesel chemical components.

14. The method according to claim 13, wherein said comparing further comprises determining a difference between said first amount and said second amount of one or more biodiesel chemical components.

* * * * *